(12) United States Patent
Lewis et al.

(10) Patent No.: US 6,964,759 B2
(45) Date of Patent: Nov. 15, 2005

(54) FORMULATIONS CONTAINING AN ANTICHOLINERGIC DRUG FOR THE TREATMENT OF CHRONIC OBSTRUCTIVE PULMONARY DISEASE

(75) Inventors: David Lewis, Parma (IT); David Ganderton, Parma (IT); Brian Meakin, Parma (IT); Gaetano Brambilla, Parma (IT); Alessandra Ferraris, Parma (IT)

(73) Assignee: Chiesi Farmaceutici S.p.A., Parma (IT)

( * ) Notice: Subject to any disclaimer, the term of this patent is extended or adjusted under 35 U.S.C. 154(b) by 0 days.

(21) Appl. No.: 10/204,307

(22) PCT Filed: Feb. 19, 2001

(86) PCT No.: PCT/EP01/01833

§ 371 (c)(1),
(2), (4) Date: Nov. 13, 2002

(87) PCT Pub. No.: WO01/62227

PCT Pub. Date: Aug. 30, 2001

(65) Prior Publication Data

US 2003/157028 A1 Aug. 21, 2003

(30) Foreign Application Priority Data

Feb. 22, 2000 (IT) .................................... MI2000A0312

(51) Int. Cl.⁷ ............................ A61K 9/12; A61K 9/72
(52) U.S. Cl. .................... 424/45; 424/434; 424/489; 514/826; 128/200.23
(58) Field of Search .......................... 424/45, 434, 489; 514/826; 128/200.23

(56) References Cited

U.S. PATENT DOCUMENTS

| | | |
|---|---|---|
| 3,361,306 A | 1/1968 | Grim |
| 3,622,053 A | 11/1971 | Ryden |
| 4,185,100 A | 1/1980 | Rovee et al. |
| 4,499,108 A | 2/1985 | Sequeira et al. |
| 4,835,145 A | 5/1989 | MacDonald |
| 5,192,528 A | 3/1993 | Radhakrishnan et al. |
| 5,415,853 A | 5/1995 | Hettche et al. |
| 5,435,297 A | 7/1995 | Klein |
| 5,605,674 A | 2/1997 | Purewal et al. |
| 5,642,728 A | 7/1997 | Andersson et al. |
| 5,653,961 A | 8/1997 | McNally et al. |
| 5,676,930 A | 10/1997 | Jager |
| 5,683,677 A | 11/1997 | Purewal et al. |
| 5,695,743 A | 12/1997 | Purewal et al. |
| 5,891,419 A | 4/1999 | Cutie |
| 5,954,047 A | 9/1999 | Armer et al. |
| 5,955,058 A | 9/1999 | Jager et al. |
| 6,004,537 A | 12/1999 | Blondino et al. |
| 6,006,745 A | 12/1999 | Marecki et al. |
| 6,026,808 A | 2/2000 | Armer et al. |
| 6,045,778 A | 4/2000 | Jager et al. |
| 6,045,784 A | 4/2000 | Ruebusch et al. |
| 6,131,566 A | 10/2000 | Ashurst |
| 6,143,277 A | 11/2000 | Ashurst et al. |
| 6,149,892 A | 11/2000 | Britto |
| 6,150,418 A | 11/2000 | Hochrainer et al. |
| 6,241,969 B1 | 6/2001 | Saidi et al. |
| 6,253,762 B1 * | 7/2001 | Britto ............... 128/200.14 |
| 6,290,930 B1 | 9/2001 | Blondino et al. |
| 6,315,985 B1 | 11/2001 | Wu et al. |
| 6,413,496 B1 * | 7/2002 | Goodman et al. ........... 424/45 |
| 6,451,285 B2 | 9/2002 | Blondino et al. |
| 6,645,466 B1 | 11/2003 | Keller et al. |
| 2003/0066525 A1 * | 4/2003 | Lewis et al. ........... 128/200.23 |
| 2003/0077230 A1 | 4/2003 | Blondino et al. |
| 2003/0157028 A1 | 8/2003 | Lewis et al. |
| 2003/0190287 A1 | 10/2003 | Lewis et al. |
| 2003/0206870 A1 | 11/2003 | Lewis et al. |
| 2004/0096399 A1 * | 5/2004 | Lewis et al. ............... 424/45 |

FOREIGN PATENT DOCUMENTS

| | | |
|---|---|---|
| EP | 0 372 777 | 6/1990 |
| EP | 0 504 112 A2 | 9/1992 |
| EP | 0 642 992 A2 | 3/1995 |
| EP | 0 653 204 | 5/1995 |
| EP | 0 911 048 | 4/1999 |
| GB | 1 525 181 | 9/1978 |
| GB | 2 326 334 | 12/1998 |
| WO | WO 91/11173 | 8/1991 |
| WO | WO 92/11236 | 7/1992 |
| WO | WO 92/20391 | 11/1992 |
| WO | WO 93/05765 | 4/1993 |
| WO | WO 93/11743 | 6/1993 |
| WO | WO 93/11747 | 6/1993 |
| WO | WO 93/18746 | 9/1993 |
| WO | 94 13262 | 6/1994 |
| WO | WO 94/14490 | 7/1994 |
| WO | WO 94/21228 | 9/1994 |
| WO | WO 94/21229 | 9/1994 |
| WO | WO 95/17195 | 6/1995 |
| WO | WO 96/18384 | 6/1996 |
| WO | WO 96/19198 | 6/1996 |
| WO | WO 96/19968 | 7/1996 |
| WO | WO 96/19969 | 7/1996 |

(Continued)

OTHER PUBLICATIONS

R.O. Williams, III et al, "A study of an epoxy aerosol can lining exposed to hydrofluoroalkane propellants", *European Journal of Pharmaceutics and Biopharmaceutics*, vol. 44, pp. 195–203, (1997).

(Continued)

*Primary Examiner*—Gary Kunz
*Assistant Examiner*—Mina Haghighatian
(74) *Attorney, Agent, or Firm*—Oblon, Spivak, McClelland, Maier & Neustadt, P.C.

(57) ABSTRACT

Formulations for the administration through pressurized metered dose aerosol inhalers containing an anticholineric drug in solution in a hydrofluorocarbon propellant, a cosolvent and a low volatility component, and the use thereof in chronic obstructive pulmonary disease.

24 Claims, No Drawings

FOREIGN PATENT DOCUMENTS

| | | |
|---|---|---|
| WO | WO 96/32099 | 10/1996 |
| WO | WO 96/32150 | 10/1996 |
| WO | WO 96/32151 | 10/1996 |
| WO | WO 96/32345 | 10/1996 |
| WO | WO 97/47286 | 12/1997 |
| WO | WO 98/01147 | 1/1998 |
| WO | WO 98/03533 | 1/1998 |
| WO | WO 98/05302 | 2/1998 |
| WO | WO 98/13031 | 4/1998 |
| WO | WO 98/24420 | 6/1998 |
| WO | WO 98/34595 | 8/1998 |
| WO | WO 98/34596 | 8/1998 |
| WO | 98 56349 | 12/1998 |
| WO | WO 99/12596 | 3/1999 |
| WO | WO 99/64014 | 12/1999 |
| WO | WO 99/65460 | 12/1999 |
| WO | WO 99/65464 | 12/1999 |
| WO | WO 00/06121 | 2/2000 |
| WO | WO 00/07567 | 2/2000 |
| WO | WO 00/23065 | 4/2000 |
| WO | 00 30608 | 6/2000 |
| WO | WO 00/35458 | 6/2000 |
| WO | WO 00/53157 | 9/2000 |
| WO | WO 00/78286 | 12/2000 |
| WO | WO 01/47493 | 7/2001 |

OTHER PUBLICATIONS

*ABPI Compendium of Data Sheets and Summaries of Product Characteristics*, Datapharm Publications Limited, London, pp. 81–82, (1996–1997).

Paul A. Sanders, Ph.D., "Homogeneous Systems and Their Properties", *Handbook of Aerosol Technology*, Second Edition, Van Nostrand Reinhold Company, NY, p. 30, 1979.

G. Brambilla et al, "Modulation of Aerosol Clouds Produced by HFA Solution Inhalers", *Portable Inhalers*, pp. 155–159, (Nov. 26 & 27, 1998).

B. Meakin, "Fine Particle Dose Control of Solution Based pMDIs", *Drug Delivery to the Lungs IX*, The Aerosol Society, pp. 1–20, (Dec. 14 & 15, 1998).

S.S. Davis, "Physico–Chemical Studies on Aerosol Solutions For Drug Delievery I. Water–Propylene Glycol Systems", *International Journal of Pharmaceutics*, 1, 1978, pp. 71–83.

L. Harrison et al, "Twenty–eight–day Double–blind Safety Study of an HFA–134a Inhalation Aerosol System in Healthy Subjects", *J. Pharm. Pharmacol.*, 1996, vol. 48, pp. 596–600.

P. Hoet et al, "Epldemic of liver disease caused by hydrochlorofluorocarbons used as ozone–sparing substitutes of chlorofluorocarbons", *The Lancet*, 1997, vol. 350, pp. 556–559.

J. Daly, Jr., "Properties and toxicology of CFC alternatives", *Aerosol Age*, Feb. 1990, pp. 26–27, 40, 56 and 57.

D. Strobach, "Alternatives to CFCs" Part II, *Aerosol Age*, Jul. 1988, pp. 32–33, 42 and 43.

Tsi–Zong Tzou et al, "Drug Form Selection in Albuterol–Containing Metered–Dose Inhaler Formulations and Its Impact on Chemical and Physical Stability", *Journal of Pharmaceutical Sciences*, 1997, vol. 86, No. 12, pp. 1352–1357.

M.J. Kontny et al, "Issues Surrounding MDI Formulation Development with Non–CFC Propellants", *Journal of Aerosol Medicine*, 1991, vol. 4, No. 3, pp. 181–187.

I. P. Tansey, "Changing to CFC–Free Inhalers: The Technical and Clinical Challenges", *The Pharmaceutical Journal*, 1997, vol. 259, pp. 896–898.

D. Tiwari et al, Compatibility Evaluation of Metered–Dose Inhaler Valve Elastomers with Tetrafluoroethane (P134a), a Non–CFC Propellant, *Drug Development and Industrial Pharmacy*, 1998, vol. 24, No. 4, pp. 345–352.

*Handbook of Pharmaceutical Excipients*, 3rd Ed., Kibbe Editor, pp. 7–9, 220–222, 234–235 and 560–561.

L. I. Harrison et al, "Pharmacokinetics and Dose Proportionality of Beclomethasone From Three Strengths of A CFC–Free Beclomethasone Dipropionate Metered–Dose Inhaler", *Biopharmaceutics & Drug Disposition*, 1997, vol. 18, No. 7, pp. 635–643.

Chet Leach, "Enhanced Drug Delivery Through Reformulating MDIs with HFA Propellants–Drug Deposition and Its Effect on Preclinical and Clinical Programs", *Respiratory Drug Delivery V*, 1996, pp. 133–144.

* cited by examiner

FORMULATIONS CONTAINING AN ANTICHOLINERGIC DRUG FOR THE TREATMENT OF CHRONIC OBSTRUCTIVE PULMONARY DISEASE

The present invention relates to formulations for administration through pressurized metered dose inhalers containing a quaternary ammonium salt with anticholinergic action in solution in a hydrofluorocarbon propellant, a cosolvent and a low volatility component. More particularly, the invention relates to formulations containing ipratropium bromide in solution, in which the concentration of active ingredient corresponds to single doses ranging from 80 to 320 μg and the amount of respirable particles is directly related to the dose itself. "Single dose" means the amount of active ingredient delivered by a single actuation of the inhaler.

The formulations of the invention can be useful for the treatment of any respiratory disease and in particular for the treatment of the chronic obstructive pulmonary disease.

The term chronic obstructive pulmonary disease (COPD) refers to a spectrum of diseases such as chronic bronchitis, asthma and lung emphysema, characterized by bronchospasm, cough, hypersecretion and dyspnea which are more and more frequent also due to tabagism as well as an increase of atmospheric pollution. Such disease has social relevance in that it involves repeated, expensive treatments.

Anticholinergic quaternary ammonium salts, such as oxitropium bromide, tiotropium bromide and ipratropium bromide, are usually prescribed in the form of inhalatory formulations, for patients suffering from said disease, due to their bronchodilating, antisecretive and bronchospasm-preventive actions.

Said drugs, particularly ipratropium bromide, induce less prompt bronchodilation than conventional β2-agonists, but provide greater peak response and longer duration of action. Said characteristics make them particularly suitable for the chronic treatment rather than the acute one (Ferguson G. et al. *N Engl J Med* 1993, 328, 1017–1022).

Although the single optimal dose for the administration of nebulized ipratropium bromide in the treatment of COPD has been established to be 0.4 mg (Gross N J et al *Am Rev Respir Dis* 1989, 139, 1188–1191), the dosage via pressurized metered dose inhalers has not yet been univocally established. Some authors (Ferguson G. et al, passim) have however suggested that treatment of said disease could benefit from use of higher doses than recommended ones (54–109 μg). Recent studies (Ikeda A et al. *Thorax* 1996, 51, 48–53; Shivaram U et al. *Resp Med* 1997, 91, 327–334; Wood F et al. *Amer J Resp Crit Care Med* 1999, 159, A 523) have demonstrated that the administration of single doses ranging from 80 to 320 μg is beneficial for the improvement in lung function, maximal workload and oxygen consumption.

Wood et al also observed for doses of at least 160 μg a longer duration of action, up to 12 hours: such prolonged effect would allow for a bis in die (b.i.d.) (twice a day) administration with evident advantages in terms of patient compliance.

The formulations currently available on the market in the form of metered dose aerosols in chlorofluorocarbons (Freon 11 and Freon 12) suspensions are able of delivering single doses of 20 or 40 μg and the recommended posology envisions the administration of 1–2 shots 3–4 times a day. Therefore, an increase of the frequency of administration to 4–6 times a day would be necessary to guarantee a higher daily dosage regimen, thus adversely affecting the patient compliance.

On the other hand, the effectiveness of an aerosol device, particularly a pressurized metered dose aerosol, is a function of the dose deposited in the peripheral tract of the pulmonary tree, that is, in turn mainly affected by the particle size distribution. The particle size is quantified by measuring a characteristic equivalent sphere diameter, known as median aerodynamic diameter (MAD). Particles having a MAD ranging from 0.8 to 5 microns (μm) are usually considered respirable, i.e. capable of being deposited into the lower airways. It has also been established that, in the case of anticholinergic drugs for use in obstructive pulmonary diseases, the optimal particle size should be approximately 3 μm (Zanen P et al. *Int. J. Pharm.* 1995, 114, 111–115; *Thorax* 1996, 51, 977–980).

In the suspension formulations, the size distribution of the delivered particles almost exclusively depends on the particle size distribution of the suspended particles, and hence on the process used for preparing them (milling or precipitation). Any kind of adjustments of the particle size of the delivered aerosol can be carried out by those skilled in the art, by suitably changing amounts and types of excipients, surface tension of the propellant, size of the metering chamber and diameter of the actuator orifice. The preparation of suspension formulations at higher concentrations of drugs aimed at delivering higher single doses could however involve problems intrinsically difficult to be solved. Under high concentration conditions, the suspended particles could, indeed, give rise to aggregation, particularly during storage, so to an increment of the size of particles. Larger size particles deposit more quickly and can give rise to the formation of compacted and fuse agglomerates (cakes) which, in turn may impair the possibility of re-suspending the product by simple agitation. Such drawback, could jeopardize both physical stability and therapeutic efficacy of the respective formulations; moreover, even after aerosolization, said cakes could turn out to be hard to be re-dispersed, so they will deposit mainly on the oropharynx tract, to the detriment of the fraction deposited on the peripheral respiratory tract (respirable fraction).

It is known that the chlorofluorocarbon propellants such as Freon 11 and Freon 12, which for many years have been the preferred propellants used in the aerosols, are being phased out and also their use in medicinal formulations, although temporarily exempted, will be banished.

Hydrofluoroalkanes (HFAs) and in particular 1,1,1,2-tetrafluoroethane (HFA 134a) and 1,1,1,2,3,3,3-heptafluoropropane (HFA 227) have been acknowledged to be the best candidates as substitutes for CFCs.

A number of documents concerning the preparation of HFA formulations of ipratropium bromide are disclosed in the prior art, for example WO 91/11495, WO 91/11496 (Boehringer), WO 93/05765 (Fisons), WO 96/19168 (Astra) and WO 98/34595 (Jago); these examples, however, relate to suspension formulations in which the active ingredient concentrations (0.08–0.1% by weight) correspond to single doses of 20–50 μg; furthermore, no data concerning physical stability during storage are provided. In other documents (EP 513217, WO 92/00107, EP 587790, EP 588897, WO 94/21228, WO 94/21229, WO 98/34596, WO 98/24420), formulations containing ipratropium bromide are only cited but not exemplified.

High-dosage suspension formulations in which CFCs are replaced with HFAs would nevertheless exhibit the same pitfalls in term of physical stability and therapeutical efficacy as mentioned above; moreover, in the case of anticholinergic quaternary ammonium salts such as ipratropium bromide, the possibility of preparing formulations of adequate physical stability during storage would further be compromised or even prevented by the partial solubility of said active ingredient in HFA (Brambilla et al. *Int J Pharm* 1999, 186, 53–61); in fact, the size of the suspended particles could grow during storage as a consequence of the partial or total recrystallization of the small amount of dissolved solute, thus worsening the problems deriving from the lack of steady particle size distribution.

In this scenario, solution compositions should unavoidably been used. Said compositions provide a number of advantages in that they are easier to be prepared and could allow to avoid the physical stability problems potentially linked to the high dosage suspension formulations. However, even solution formulation are not rid of potential drawbacks as they can give rise, for instance, to more severe problems of chemical instability. Furthermore, since the suspended particles no longer contribute to the total volume, the problem of ensuring a direct relationship between increase in dosage and increase in the drug deposited at the therapeutical site (respiratory tract) is even more dramatic. The preparation of homogeneous solution formulations requires indeed the addition of cosolvents such as ethanol which, due to their vapor pressure higher than the propellant, increase, proportionally to their concentration, the velocity of the aerosol droplets leaving the actuator orifice. The high velocity droplets extensively deposit into the oropharyngeal tract to the detriment of the dose which penetrates into the lower airways. The higher the dosage of the drug the higher is the amount of cosolvent necessary to solubilise, and hence the lesser is the percentage of therapeutically effective droplets (respirable dose).

In consideration of the therapeutical requirements outlined above and problems thereof, it would be highly advantageous to provide solution formulations comprising an anticholinergic drug, such as ipratropium bromide to be used with pressurised metered dose inhalers, in which the active ingredient concentration corresponds to single doses ranging from 80 to 320 $\mu$g, characterized by adequate chemical stability for pharmaceutical use and capable of providing, on actuation, an amount of respirable particles directly proportional to the delivered dose. Said formulations would turn out to be useful for the treatment of respiratory ailments such as chronic obstructive pulmonary disease.

The object of the present invention is to provide solution formulations comprising an anticholinergic quaternary ammonium salt selected from oxitropium bromide, tiotropium bromide and especially ipratropium bromide, to be used with pressurized metered dose inhalers for the treatment of COPD, said solutions being chemically stable and capable of:
i) delivering high single doses, of at least 60 $\mu$g and preferably 80 $\mu$g;
ii) provide an amount of respirable particles directly proportional to the delivered dose;
iii) allow b.i.d. administration with evident advantages in terms of patient compliance.

In the formulations of the invention, to make the transition from CFC formulations to HFA formulations easier, the respirable fraction can favorably correspond to that of the CFC suspension formulations presently available on the market.

According to a first embodiment of the invention, there is provided a solution formulation comprising from 0.11% to 1.14% by weight of an anticholinergic quaternary ammonium salt and a carrier consisting of a hydrofluoroalkane propellant, a cosolvent and a low volatility component that also has solvent properties.

In a preferred embodiment the hydrofluoroalkane propellant is HFA 134a, the cosolvent is ethanol and the low volatility component is glycerol.

According to a more particular embodiment of the invention, there is provided a solution formulation comprising from 0.14%–0.28% by weight of ipratropium bromide and a carrier consisting of HFA 134a as a propellant, 13% by weight of ethanol and 1% by weight of glycerol.

In WO 98/56349 the Applicant disclosed solution compositions for use in an aerosol inhaler, comprising an active ingredient, a propellant containing a hydrofluoroalkane (HFA), a cosolvent and further comprising a low volatility component to increase the median aerodynamic diameter (MAD) of the aerosol particles on actuation of the inhaler; the examples concerning ipratropium bromide however refer to formulations in which the active ingredient concentrations corresponded to the usual single doses (20–40 $\mu$g). Said formulations proved to be pharmaceutically equivalent to the presently marketed formulations, consisting of CFC suspensions (Ganderton D et al. J. Aerosol Med. 1999, 12, 119).

It has now been found that by using a low volatility component with suitable solvent power for the active ingredient, homogeneous solution formulations are obtained even in the presence of concentrations of an anticholinergic quaternary ammonium salt comprised between 0.11% and 1.14% by weight (which equates to 0.11–1.14 g of active ingredient per 100 g of formulation). In particular, it is possible to prepare homogeneous solution formulations in the presence of 0.14%–0.28% by weight ipratropium bromide corresponding to single doses ranging from 80 to 320 $\mu$g.

The use of a low volatility component allows to minimize the amount of cosolvent, in this case ethanol, added to the formulation and hence to avoid the negative effects on the respirable/therapeutically effective dose due to the increase of its relative percentage.

In the formulations of the invention, the median aerodynamic diameter (MAD) of the droplets remains substantially unchanged at increasing concentrations, therefore the respirable dose is directly related to the dose obtained on actuation of the inhaler. As a consequence, the increase in the respirable fraction concentration remains steady. Contrary to what reported in the prior art (Dolovich M Aerosol Science and Technology 1995, 22, 392–399) it has in fact surprisingly been found that in the formulations of the invention the respirable fraction does not decrease as the single dose increases. Furthermore, by suitably adjusting the actuator orifice diameter, it is possible, as the delivered dose increases, to steadily increase the respirable dose so that this is also linearly related to the dose of the CFC suspension formulations presently available on the market. Said feature makes the formulations of the invention therapeutically preferable as they avoid possible problems related to a non-linear response, such as accumulation, greater side effects or vice versa less effective therapeutical action.

WO 94/13262 generically disclosed and claimed aerosol HFA solution formulations comprising 0.001%–2.5% of ipratropium bromide in the presence of ethanol as cosolvent and of small amounts of organic or inorganic acids. The specific examples however only relate to formulations with active ingredient concentrations (0.0187%–0.0748% by weight) corresponding to doses for single actuation ranging from 10 to 40 $\mu$g and containing 15% by weight of ethanol. Furthermore, organic or inorganic acids are used for ensuring higher chemical stability of the active ingredient, and not for solving the technical problem related with the preparation of high dosage formulations providing a respirable dose therapeutically effective and directly related to the concentration.

The Applicant has also proved that formulations prepared according to the teaching of said application, with high concentrations of ipratropium bromide, require the use of ethanol in remarkable percentages which significantly jeopardize the performances in terms of respirable fraction. It has been indeed demonstrated that, in solution formulation only consisting of HFA as a propellant and ethanol as a co-solvent, the amount of ethanol necessary to solubilize ipratropium bromide in concentrations corresponding to single doses ranging from 80 to 160 µg is of at least about 19% by weight. On the other hand, formulations containing such a large amount of ethanol, of at least 19% by weight, give rise to a reduced respirable dose and a decrease in the MAD.

The formulations of the invention can be prepared as described in WO 98/56349 and comprise a quaternary ammonium salt provided of anticholinergic action, such as oxitropium bromide, tiotropium bromide, ipratropium bromide in a concentration that, depending on the characteristics of the active ingredient, ranges from 0.11% to 1.14% by weight and which, in turn, could give rise, by suitably adjusting the volume of the metering chamber, to single doses ranging from 60 to 640 µg. More preferably, the active ingredient is a quaternary ammonium salt provided with anticholinergic action in a concentration ranging from 0.12% to 0.56% by weight.

Even more preferably, the active ingredient is ipratropium bromide in a concentration ranging from 0.14% to 0.28% by weight. According to the volume of the metering chamber, the formulation containing 0.14% ipratropium bromide can be used for delivering single doses of 80 and 160 µg, while that containing 0.28% for single doses of 160 and 320 µg. Advantageously, the low volatility component has a vapor pressure at 25° C. not above 0.1 kPa, preferably not above 0.05 pKa. Particularly suitable for the use of the invention are glycols, in particular propylene glycol, polyethylene glycol and most preferably glycerol. However, the invention also comprises all the substances, alone or in admixture, having similar vapor pressure characteristics and suitable solvent power for the active ingredients belonging to the anticholinergic quaternary ammonium salts. The composition preferably contains at least 0.2%, more preferably 1% by weight of said component and anyway no more than 6%.

The cosolvent has advantageously higher polarity than the propellant and is preferably an alcohol, more preferably ethanol. In this case, the amount of cosolvent in the composition is below 19% by weight, preferably it does not exceed 15% by weight more preferably it does not exceed 13% by weight.

All the percentages are expressed as gram per 100 g of formulation.

Preferred hydrofluoroalkane propellants are HFA 134a, HFA 227 or mixtures thereof.

The formulations of the invention are preferably stored in pressurized inhalers for aerosol, part or all of their inner metal surfaces being made of anodized aluminium, stainless steel or coated with an inert organic coating agent. It has, in fact, been observed that in this type of cans the active ingredient remains chemically stable during storage, even at concentrations higher than 0.11% by weight. The inhalers can be equipped with any suitable conventional or unconventional dispensing valve, preferably a metered dose valve as well as any suitable conventional or unconventional metering chamber. Advantageously, the inhalers are equipped with an actuator with orifice diameter from 0.25 to 0.50 mm, preferably 0.3 mm and with a metering chamber with a volume from 25 µl to 100 µl. However, the volume of metering chamber and the orifice diameter of the actuator will be suitably selected by the person skilled in order to deliver the desired single dose as well as to the best performances in term of respirable dose.

The invention refers also to a process for the preparation of pharmaceutical formulations according to claims 1–6 which consists in filling the components into the metered dose inhaler in the following order: active ingredient, low volatility component, cosolvent and finally propellant through the valve.

Finally, the invention relates to, the use of said formulations in the treatment of bronchopulmonary diseases, in particular chronic obstructive pulmonary disease.

Specific embodiments of the invention are described in detail in the following.

EXAMPLE 1

Ipratropium Bromide Aerosol Solution Formulation in a Carrier Constituted of HFA 134a as a Propellant, Ethanol as a Co-Solvent and Glycerol as a Low Volatility Component The aerosol formulations of the invention described below are prepared according to the following method. The components necessary to the formulation are transferred into 12 ml aerosol cans in the following order: drug, low volatility component, absolute ethanol.

After crimping the valve onto the can, the propellant is added through the valve. The weight gain of the can after addition of each component is recorded to evaluate the weight percentage of each component in the formulation.

| | Amounts | | |
|---|---|---|---|
| | Per unit | | Dose of a single actuation |
| Components | mg | % by weight | µg |
| Ipratropium bromide | 19.2–38.4 | 0.14–0.28 | 80–320 |
| Absolute ethanol | | 13 | — |
| Glycerol | | 1 | — |
| HFA 134a q.s. to | 13714 | — | — |

The aerodynamic particle size distribution of each tested formulation was characterized using a Multistage Cascade Impactor according to the procedure described in European Pharmacopoeia $2^{nd}$ edition, 1995, part V.5.9.1, pages 15–17. In this specific case, an Andersen Cascade Impactor (ACI) was used.

Results were obtained as a mean of 3–4 cans. For each device, 5–25 cumulative actuations were carried out after discarding the first 5.

Deposition of the drug on each ACI plate was determined by high pressure liquid chromatography (HPLC). Mean metered dose was calculated from the cumulative deposition in the actuator and ACI (stages); mean delivered dose was calculated from the cumulative deposition in the ACI. Mean respirable dose (fine particle dose) was obtained from the deposition on Stages 3 to filter corresponding to particles $\leq 4.71$ µm, divided by the number of actuations per experiment.

MAD and associated GSD (standard geometric deviation) values were obtained from probit transformation of cumulative percent undersize—log (ACI effective cut-off particle size diameter) and linear regression analysis of the resultant data, (Ph. Eur. Supp 1999).

The delivery characteristics of formulations containing increasing amounts of ipratropium bromide present in cans equipped with standard Bespack BK 360 actuators with 0.3 mm orifice diameter and a metering chamber volume of 50 μl are reported in Table 1. The use of a metering chamber volume of 100 μl allows a 320 μg strength variant of the 160 μg formulation.

It can be observed that MAD is substantially unaffected by the active ingredient concentration, so that the amount of droplets with size lower than 4.7 μm (respirable dose) is linearly related to the nominal dose.

Only at a nominal dose of 320 μg, a slight decrease of the respirable fraction is observed.

standard aerosol cans. The components are expressed as percentages by weight of the total formulation. Visual appearance of all manufactured formulations is assessed using a polarized light source immediately after preparation and again after 3 weeks storage at 4.0±0.4° C. Observations where further confirmed after 10 months storage at 4.0±0.4° C.

Ipratropium bromide is found to crystallise for the following ethanol levels (% by weight): 14.7, 15.0, 16.8, 17.2, 17.5, 17.9 while is found not to crystallise for the following ethanol levels: 18.9, 19.2, 20.6, 21.0, 21.3, 22.2, 22.6, 23.0, 23.4, 24.5, 29.7, 38.9, 40.1.

Therefore about 19% by weight of ethanol is required to solubilise an amount of ipratropium bromide (0.14% by weight) which could give rise, by suitably selecting the volume of the metering chamber, to single doses of 80 and 160 μg within a HFA 134a formulation.

TABLE 1

Performances of formulations containing as active ingredient ipratropium bromide at different concentrations, such as to give raise to the reported nominal doses.

| Nominal Dose[1] (μg) | Metered dose[2] (μg) | Delivered dose[3] (μg) | Respirable dose[4] (μg) | Respirable fraction[5] (%) | MAD (μm) | GSD |
|---|---|---|---|---|---|---|
| 20 | 20.6 ± 1.6 | 18.8 ± 1.6 | 6.8 ± 1.1 | 33.3 ± 3.8 | 2.4 ± 0.3 | 2.1 ± 0.8 |
| 40 | 42.2 ± 1.8 | 38.7 ± 1.9 | 11.7 ± 1.2 | 31.5 ± 3.8 | 2.2 ± 0.1 | 2.1 ± 0.1 |
| 80 | 78.5 ± 0.4 | 72.7 ± 0.6 | 23.3 ± 4.5 | 32.0 ± 6.1 | 2.7 ± 0.3 | 2.2 ± 0.1 |
| 160 | 161.1 ± 12.5 | 149.2 ± 10.7 | 45.2 ± 2.5 | 30.4 ± 3.5 | 2.5 ± 0.2 | 2.3 ± 0.1 |
| 320 | 321.4 ± 2.0 | 290.5 ± 1.9 | 73.2 ± 3.0 | 25.2 ± 1.2 | 2.9 ± 0.2 | 2.6 ± 0.1 |

[1]Nominal dose: theoretical dose per single actuation
[2]Metered dose: sum of the dose delivered through the device plus the active ingredient residue deposited on the device actuator.
[3]Delivered dose: amount of active particles deposited into the various ACI stages
[4]Respirable dose (fine particle dose): amount of active particles of size less than 4.7 μm
[5]Respirable fraction (fine particle fraction): ratio between the delivered dose and the respirable dose.

EXAMPLE 2

Ipratropium Bromide Aerosol Solution Formulation in HFA 134a as a Propellant and Ethanol as a Co-Solvent Determination of the Solubility of Ipratropium Bromide in Ethanol 20.1±0.2 mg of ipratropium bromide is weighed into Saint-Gobain aerosol bottles.

Increased volumes of absolute ethanol are added to the same aerosol bottle using a Gilson variable pipette.

A Bespak BK357 valve is crimped onto the same aerosol bottle. Shaking and ultra-sonication ensured a homogeneous solution was formed before a pre-determined mass of HFA 134a is filled through the valve.

The individual weight of ipratropium bromide, ethanol, and HFA134a addition is recorded using a four-figure analytical balance.

Final formulations have a total volume into cans having a volume of 12±0.3 ml (20° C.), corresponding to that of the The formula of the corresponding composition is reported below.

| | Amount | | |
|---|---|---|---|
| | Per unit | | Dose of a single actuation |
| Components | mg | % by weight | μg |
| Ipratropium bromide | 20.1 | 0.14 | 80–160 |
| Absolute ethanol | 2735 | 19 | — |
| HFA 134a q.s. to | 14397 | — | — |

Delivery performances of the HFA formulations corresponding to single nominal doses of 80 and 160 μg The delivery characteristics of the formulation in cans equipped with standard Bespack BK 360 actuators with 0.3 mm orifice diameter and a metering chamber volume of 50

μl are reported in Table 2. The use of a metering chamber volume of 100 μl allows a 160 μg strength variant of the 80 μg formulation.

The relevant parameters were determined as described in Example 1.

It can be observed that, the formulation containing an ethanol level of 19% by weight depresses the respirable dose (≦4.7 μm); it also reduces the MAD from 2.2–2.9 μm to 1.2–1.3 μm; and increases the Geometric Standard Deviation (GSD) from 2.1–2.6 to 4.3–6.2.

TABLE 2

Performances of a the formulation without the low volatility component containing as active ingredient ipratropium bromide corresponding to nominal doses of 80 and 160 μg.

| Nominal Dose (μg) | Metered dose (μg) | Delivered dose (μg) | Respirable dose (μg) | Respirable fraction (%) | MAD (μm) | GSD |
|---|---|---|---|---|---|---|
| 80 | 76.6 ± 1.6 | 70.0 ± 1.0 | 20.0 ± 1.3 | 28.7 ± 1.5 | 1.2 ± 0.1 | 4.3 ± 0.4 |
| 160 | 158.5 ± 2.0 | 144.2 ± 1.7 | 31.4 ± 1.3 | 21.8 ± 1.1 | 1.3 ± 0.2 | 6.2 ± 0.2 |

What is claimed is:

1. A metered dose inhaler which upon actuation dispenses a dose of an anticholinergic ammonium compound ranging from 60 to 640 μg, and which contains a solution comprising:
   at least one solubilized anticholinergic quaternary ammonium compound in an amount ranging from 0.11–1.14 wt. %,
   at least one hydrofluoroalkane propellant,
   15 wt. % or less of a cosolvent which is at least one alcohol having higher polarity than the propellant, and
   at least one low volatility component which has a vapor pressure at 25° C. not more than 0.1 kPa.

2. The metered dose inhaler of claim 1, wherein the anticholinergic compound is ipratropium bromide.

3. The metered dose inhaler of claim 1, wherein the anticholinergic compound is ipratropium bromide in a concentration ranging from 0.14 to 0.28% by weight.

4. The metered dose inhaler of claim 1, wherein the anticholinergic compound is oxitropium bromide or tiotropium bromide.

5. The metered dose inhaler of claim 1, wherein the hydrofluroalkane propellant is HFA 134a, HFA 227 or mixtures thereof.

6. The metered dose inhaler of claim 1, wherein the cosolvent contains ethanol.

7. The metered dose inhaler of claim 1, wherein the cosolvent does not contain ethanol.

8. The metered dose inhaler of claim 1, wherein the solution contains 0.2% to 6% of the low volatility component.

9. The metered dose inhaler of claim 1, wherein the low volatility component is propylene glycol, polyethylene glycol or glycerol, or admixtures thereof.

10. The metered dose inhaler of claim 1, in which the propellant is HFA 134a, the low volatility component is glycerol and the cosolvent is ethanol.

11. The metered dose inhaler of claim 1, wherein said solution contains 13% by weight ethanol as the cosolvent and 1% by weight glycerol as the low volatility component.

12. The metered dose inhaler of claim 1, wherein the solution consists essentially of:
   one or more anticholinergic quaternary ammonium compound(s) in an amount ranging from 0.11–1.14 wt. %,
   at least one hydrofluoroalkane propellant,
   15 wt. % or less of a cosolvent, which cosolvent is one or more alcohol(s) having higher polarity than the propellant, and
   0.2% to 6% of one or more low volatility component(s).

13. The metered dose inhaler of claim 1, wherein part or all of the inner metal surface(s) are made of anodized aluminum, stainless steel or are coated with an inert organic coating agent.

14. The metered dose inhaler of claim 1, which is equipped with an actuator with an orifice diameter ranging from 0.25 to 0.5 mm.

15. The metered dose inhaler of claim 1, which comprises a metering chamber with a volume ranging from 25 μl to 100 μl.

16. A method for treating bronchospasm, cough, hypersecretion, or dyspnea comprising administering to a subject in need thereof a dose of an anticholinergic ammonium compound ranging from 60 to 640 μg from the inhaler of claim 1.

17. A method for treating a bronchopulmonary disease or a chronic obstructive pulmonary disease comprising administering to a subject in need thereof a dose of an anticholinergic ammonium compound ranging from 60 to 640 μg from the inhaler of claim 1.

18. The method of claim 17, wherein said disease is chronic bronchitis.

19. The method of claim 17, wherein said disease is asthma.

20. The method of claim 17, wherein said disease is emphysema.

21. A process for making the metered dose inhaler of claim 1, comprising:
   filling through a value the components forming said solution into the metered dose inhaler in the following order: anticholinergic compound(s), low volatility component(s), cosolvent(s) and finally propellant(s).

22. A composition comprising:
   at least one solubilized anticholinergic quaternary ammonium compound in an amount ranging from 0.11–1.14 wt. %,
   at least one hydrofluoroalkane propellant,
   15 wt. % or less of a cosolvent which is at least one alcohol having higher polarity than the propellant, and
   0.2% to 6% of at least one low volatility component which has a vapor pressure at 25° C. not more than 0.1 kPa.

23. The composition of claim 22, wherein the anticholinergic compound is ipratropium bromide in a concentration ranging from 0.14 to 0.28% by weight.

24. A fine particle dose of at least one anticholinergic quaternary ammonium compound obtained from an aerosol of the composition of claim 22, wherein at least 30% of said fine particles have a size less than 4.7 μm.

* * * * *